(12) United States Patent
Abe et al.

(10) Patent No.: US 8,998,405 B2
(45) Date of Patent: Apr. 7, 2015

(54) TRANSPORTATION DEVICE AND RECORDING APPARATUS

(71) Applicant: Seiko Epson Corporation, Tokyo (JP)

(72) Inventors: Takahiro Abe, Shiojiri (JP); Mitsutaka Ide, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/069,144

(22) Filed: Oct. 31, 2013

(65) Prior Publication Data

US 2014/0125729 A1    May 8, 2014

(30) Foreign Application Priority Data

Nov. 2, 2012  (JP) ................................ 2012-242450

(51) Int. Cl.
*B41J 11/00* (2006.01)
*B41J 11/42* (2006.01)
*B41J 15/04* (2006.01)

(52) U.S. Cl.
CPC .............. *B41J 11/0095* (2013.01); *B41J 11/42* (2013.01); *B41J 15/04* (2013.01)

(58) Field of Classification Search
USPC .......................................... 347/104, 218, 264
See application file for complete search history.

(56) References Cited

U.S. PATENT DOCUMENTS

| 6,622,625 | B1 * | 9/2003 | Sugiyama ...................... 101/484 |
|---|---|---|---|
| 6,627,872 | B1 | 9/2003 | FuKamura et al. |
| 2002/0071190 | A1 | 6/2002 | Wada et al. |
| 2007/0121176 | A1 * | 5/2007 | Yamazaki et al. ............ 358/474 |
| 2013/0127943 | A1 * | 5/2013 | Abe .................................. 347/16 |
| 2013/0135407 | A1 * | 5/2013 | Abe ................................ 347/102 |
| 2013/0141487 | A1 * | 6/2013 | Abe .................................. 347/16 |
| 2014/0118450 | A1 * | 5/2014 | Abe et al. ...................... 347/102 |
| 2014/0132687 | A1 * | 5/2014 | Abe et al. ...................... 347/104 |
| 2014/0168294 | A1 * | 6/2014 | Abe et al. .......................... 347/2 |

FOREIGN PATENT DOCUMENTS

| EP | 1213150 | 6/2002 |
|---|---|---|
| EP | 1791342 | 5/2007 |
| JP | 09-181397 | 7/1997 |
| JP | 2000-230856 | 8/2000 |
| JP | 2002-196208 | 7/2002 |
| JP | 2007-217176 | 8/2007 |
| JP | 2008-109251 | 5/2008 |
| JP | 2010-183497 | 8/2010 |

OTHER PUBLICATIONS

European Search Report for European Patent Application No. 13191463.2 dated Jan. 21, 2014.

* cited by examiner

*Primary Examiner* — Huan Tran
(74) *Attorney, Agent, or Firm* — Workman Nydegger

(57) ABSTRACT

A transportation device includes: a transportation section that transports a continuous paper; and an imaging unit that detects a transportation amount of the continuous paper which is transported by the transportation section. The imaging unit includes a lens barrel; a light irradiation unit disposed in the lens barrel and capable of radiating light on the continuous paper; a condensing lens which is disposed in a position farther than the light irradiation section with respect to the continuous paper in the lens barrel and condenses a reflected light when the light is radiated from the light irradiation section to the continuous paper; and an imaging element which is disposed in a position farther than the condensing lens with respect to the continuous paper P in the lens barrel and captures an image by receiving the reflected light condensed by the condensing lens.

8 Claims, 2 Drawing Sheets

TRANSPORTATION DEVICE AND RECORDING APPARATUS

BACKGROUND

1. Technical Field

The present invention relates to a transportation device transporting an object to be detected such as a paper which is used, for example, in printing or the like and a recording apparatus including the transportation device.

2. Related Art

In the related art, as a type of recording apparatus, an ink jet type printer is disclosed which forms an image by ejecting ink from a recording head (a recording section) to a recording paper (an object to be detected) (for example, JP-A-2007-217176).

A printer disclosed in JP-A-2007-217176 includes a photographing device (a detection section) having a light emitting element (a light irradiation section) and an imaging element (an imaging section) which has an optical system (an optical member). Then, a surface texture of the recording paper which is transported is imaged as a continuous image by the photographing device. A moving amount of a target pattern in each image is calculated by comparing two images which are captured before and after for chronological order. An actual transportation amount of the recording paper is calculated by integrating the moving amount thereof. In addition, usually, the photographing device described above has a lens barrel (a case). A light emitting element and an imaging element having the optical system are disposed in the lens barrel.

However, in the photographing device of the printer described above, it is not considered particularly that the lens barrel is extended by an increase in an ambient temperature thereof. Thus, when the lens barrel is extended by the increase in the ambient temperature, since a positional relationship between the optical system and the imaging element is out of order, there is a problem that a focus position of the optical system is shifted and then imaging accuracy of the recording paper is degraded due to the imaging element.

SUMMARY

An advantage of some aspects of the invention is to provide a transportation device and a recording apparatus in which it is possible to suppress the degradation of the imaging accuracy of an object to be detected by an imaging section when a case is extended by an increase in an ambient temperature.

Hereinafter, the following means of the invention and the operation, and effects thereof will be described.

According to an aspect of the invention, there is provided a transportation device including: a transportation section that transports an object to be detected; and a detection section that detects a transportation amount of the object to be detected which is transported by the transportation section, in which the detection section includes: a case; a light irradiation section disposed in the case and capable of radiating light on the object to be detected; an optical member which is disposed in a position farther than the light irradiation section from the object to be detected in the case and condenses a reflected light when the light is radiated from the light irradiation section to the object to be detected; and an imaging section which is disposed in a position farther than the optical member from the object to be detected in the case and captures an image by receiving the reflected light condensed by the optical member, and in which the case is fixed to a position closer to the object to be detected than the optical member.

In this configuration, when the ambient temperature of the detection section is increased, since the case is extended from the fixed position as a base point, the optical member and the imaging section are moved together away from the object to be detected due to the extension of the case. Thus, even when the case is extended due to the increase in the ambient temperature, since change in the positional relationship between the optical member and the imaging section is suppressed, it is possible to suppress the shift of the focus position of the optical member. Therefore, it is possible to suppress the degradation of the imaging accuracy of the object to be detected due to the imaging section.

In the transportation device, it is preferable that the case be configured by bonding a plurality of members, and a coefficient of linear expansion of each of the members be the same as the others.

In this configuration, when the ambient temperature of the detection section is increased, each of the members configuring the case is extended in the same proportion as each other. Thus, since the positional relationship between the optical member and the imaging section is maintained, it is possible to suppress the shift of the focus position of the optical member. Therefore, even when the case is configured by bonding a plurality of members, it is possible to suppress the degradation of the imaging accuracy of the object to be detected due to the imaging section.

In the transportation device, it is preferable that each of the members be configured of the same material as each other.

In this configuration, it is possible to easily conform the coefficient of linear expansion of each of members.

In the transportation device, it is preferable that the case be fixed to a position where a distance from the object to be detected is the same as a distance between the object to be detected and the light irradiation section.

In this configuration, when the ambient temperature of the detection section is increased, since the case is extended from the position where the case is fixed as the base point, it is possible to reduce the moving amount of the light irradiation section depending on the extension of the case. Therefore, since the change in the distance between the light irradiation section and the object to be detected can be suppressed, it is possible to suppress the degradation of irradiation accuracy of the light with respect to the object to be detected due to the light irradiation section.

According to another aspect of the invention, there is provided a recording apparatus including: the transportation device having the configuration described above; and a recording section that performs a recording process with respect to the object to be detected which is transported by the transportation device.

In this configuration, it is possible to obtain the same operational advantage as the transportation device.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment in which a recording apparatus is embodied in an ink jet type printer will be described with reference to drawings.

Figure 1:
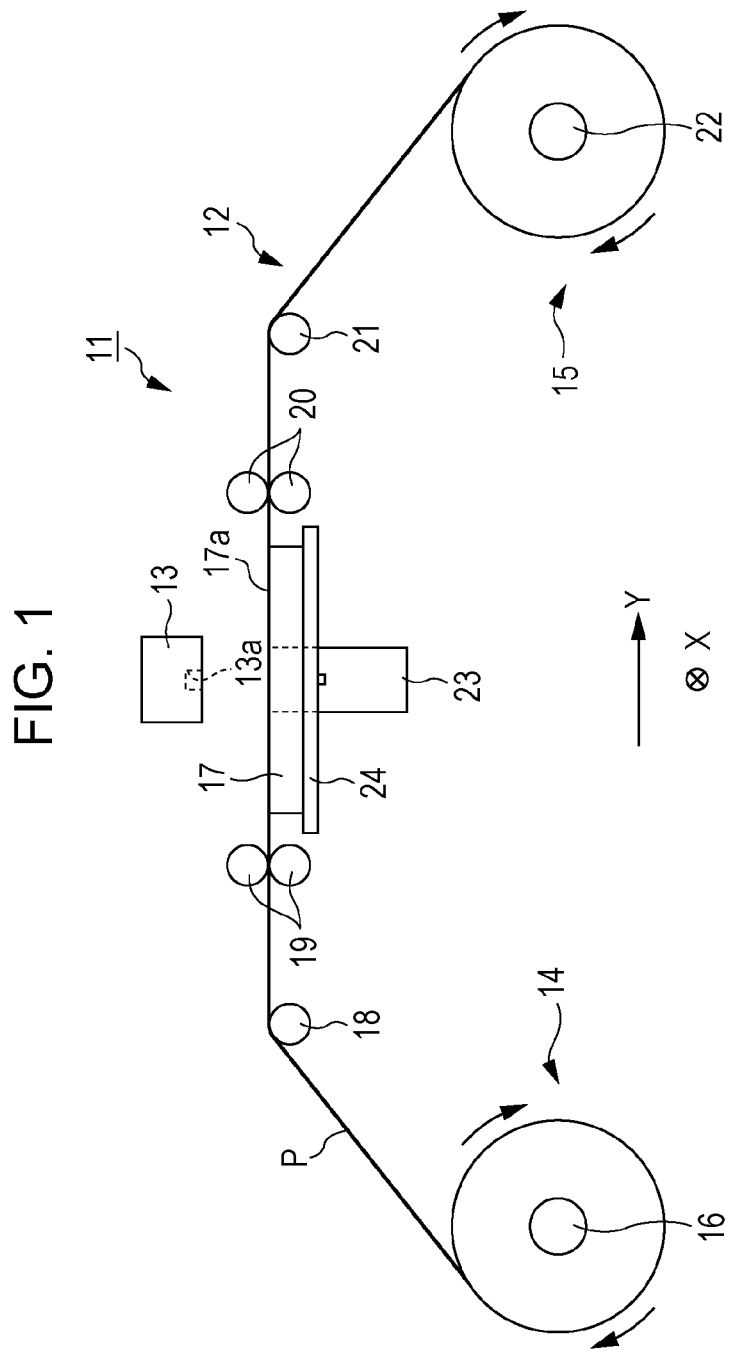
FIG. 1 is a schematic configuration view of an ink jet type printer of an embodiment.

As illustrated in FIG. 1, an ink jet type printer 11 as an example of the recording apparatus includes a transportation device 12 transporting a long sheet-shaped continuous paper P as an example of an object to be detected and a recording head 13 as an example of a recording section performing printing (recording process) by ejecting ink (liquid) with respect to the continuous paper P transported by the transportation device 12. The transportation device 12 includes a reel-out section 14 reeling out the continuous paper P and a winding section 15 winding the continuous paper P which is reeled out from the reel-out section 14 and on which the printing is performed by the recording head 13.

In other words, in FIG. 1, the reel-out section 14 is disposed in a position of a left side that is an upstream side in a transportation direction Y (rightward in FIG. 1) in the continuous paper P and the winding section 15 is disposed in a position of a right side that is a downstream side. Then, the recording head 13 is disposed in a position between the reel-out section 14 and the winding section 15 so as to face a transportation path of the continuous paper P. A plurality of nozzles 13a are formed on a surface facing the transportation path of the continuous paper P in the recording head 13 to eject the ink on the continuous paper P which is transported.

In addition, a rectangular plate-shaped support frame 24 made of metal is horizontally disposed in a position facing the recording head 13 across the transportation path of the continuous paper P. A support stand 17 made of synthetic resin, which supports an area where the printing is performed by the recording head 13 on the continuous paper P, is horizontally supported on the support frame 24 so as to face the recording head 13 across the transportation path of the continuous paper P. Then, a horizontal support surface 17a supporting the continuous paper P is a surface facing the recording head 13 in the support stand 17.

A reel-out shaft 16 extending in a width direction X (a direction orthogonal to the plane of the paper in FIG. 1) of the continuous paper P orthogonal to the transportation direction Y of the continuous paper P is rotatably provided in the reel-out section 14. The continuous paper P is integrally rotatable and is supported by the reel-out shaft 16 in a state where the continuous paper P is wound on the reel-out shaft 16 in advance in a roll shape. Then, the continuous paper P is reeled out from the reel-out shaft 16 to the downstream side of transportation path thereof by rotation of the reel-out shaft 16.

A first relay roller 18 is rotatably disposed obliquely above the right side of the reel-out shaft 16 to guide the continuous paper P to the recording head 13 side by winding and holding the continuous paper P which is reeled out from the reel-out shaft 16. A feeding roller pair 19 is disposed on the downstream side of the first relay roller 18 in the transportation path of the continuous paper P to guide the continuous paper P transported from the first relay roller 18 side on the support stand 17 while clamping the continuous paper P by rotation of the feeding roller pair 19.

A discharging roller pair 20 is disposed on the downstream side of the support stand 17 in the transportation path of the continuous paper P to guide a printed area on the continuous paper P from on the support stand 17 to the downstream side of the transportation path of the continuous paper P while clamping the continuous paper P by rotation of the discharging roller pair 20.

A second relay roller 21 is rotatably disposed on the downstream side of the discharging roller pair 20 in the transportation path of the continuous paper P to guide the continuous paper P which is transported from the discharging roller pair 20 side to the winding section 15 by winding and holding the continuous paper P. The winding section 15 is positioned obliquely below the right side of the second relay roller 21.

A winding shaft 22 extending in the width direction X of the continuous paper P orthogonal to the transportation direction Y of the continuous paper P is rotatably provided in the winding section 15. Then, the printed continuous paper P which is transported from the second relay roller 21 side is sequentially wound on the winding shaft 22 by rotation of the winding shaft 22.

Figure 2:
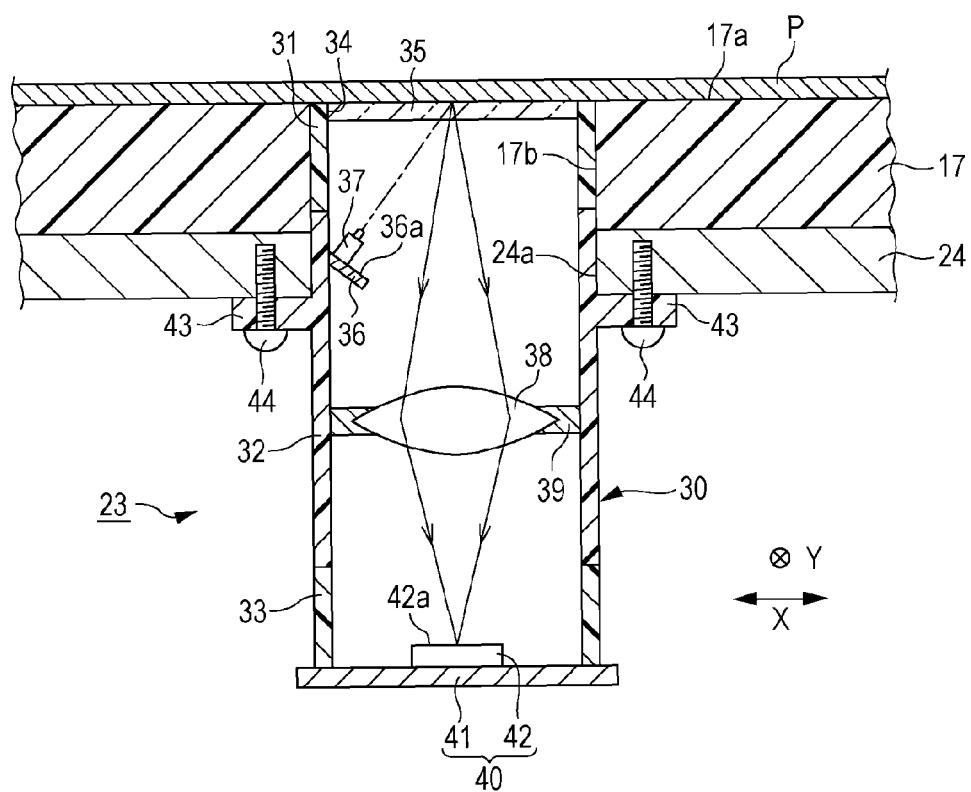
FIG. 2 is a schematic cross-sectional view of an imaging unit of the printer.

As illustrated in FIGS. 1 and 2, a through hole 17b is formed in the support stand 17 and a through hole 24a is formed in the support frame 24. The through hole 17b and the through hole 24a are overlapped in the vertical direction and have the same shape as each other. Then, an imaging unit 23 as an example of a detection section for detecting a transportation amount of the continuous paper P in a non-contact manner is fixed to the support frame 24 in a state where an upper end portion thereof is inserted into the through hole 17b and the through hole 24a. The imaging unit 23 has a control circuit (not illustrated) performing control of whole imaging unit 23.

Furthermore, in the embodiment, a transportation section transporting the continuous paper P is configured of the feeding roller pair 19 and the discharging roller pair 20.

Next, a configuration of the imaging unit 23 will be described in detail.

As illustrated in FIG. 2, the imaging unit 23 includes a lens barrel 30 made of a synthetic resin extending in the vertical direction (axial direction) as an example of a case. The lens barrel 30 is configured of a plurality (three in the embodiment) of members lined in the vertical direction by bonding the members using screws (not illustrated). Then, each member configuring the lens barrel 30 is a first lens barrel member 31, a second lens barrel member 32 and a third lens barrel member 33 sequentially from above, respectively.

The first lens barrel member 31, the second lens barrel member 32 and the third lens barrel member 33 are configured of the same material as each other. Therefore, the first lens barrel member 31, the second lens barrel member 32 and the third lens barrel member 33 have the same coefficient of linear expansion as each other. The first lens barrel member 31 and the third lens barrel member 33 have substantially the same length in the vertical direction as each other. The second lens barrel member 32 has a length of approximately three times that of the first lens barrel member 31 in the vertical direction.

The first lens barrel member 31 is disposed in the through hole 17b. A bonding surface between the first lens barrel member 31 and the second lens barrel member 32 is positioned in the through hole 17b. An upper end of the first lens barrel member 31 is the same surface as the support surface 17a of the support stand 17. A rectangular-shaped opening section of the upper end of the first lens barrel member 31 is a detection window 34 through which light is transmitted and a translucent glass 35 is fitted in the detection window 34.

An upper surface of the translucent glass 35 is disposed in a position which is slightly lower than the support surface 17a. In other words, the translucent glass 35 and the continuous paper P are disposed so as to face in the vertical direction in a state where a small gap is interposed between the translucent glass 35 and the continuous paper P which is transported on the support surface 17a. Therefore, the translucent glass 35 does not come in contact with the continuous paper P.

As illustrated in FIG. 2, a rectangle-shaped support plate 36 is provided on one side of an inner peripheral surface of the upper end portion of the second lens barrel member 32 in the width direction X of the continuous paper P. A light irradiation section 37 is mounted on a mounting surface 36a that is a surface of the detection window 34 side in the support plate 36.

In the embodiment, the light irradiation section 37 is configured of a light emitting diode (LED) and light is radiated from a lower surface side (a non-printing surface side) opposite to the printing surface of the continuous paper P which is transported on the support surface 17a through the translucent glass 35. In this case, the light irradiation section 37 is disposed so that light is obliquely radiated from the width direction X side to the lower surface (the non-printing surface) of the continuous paper P.

In addition, a condensing lens 38 as an example of an optical member is provided in a position farther than the light irradiation section 37 with respect to the continuous paper P in the lens barrel 30, in other words, in a position lower than the light irradiation section 37 in the second lens barrel member 32. The condensing lens 38 is held on an inner peripheral surface of the second lens barrel member 32 through a holding member 39. After the light, which is emitted from the light irradiation section 37 and penetrates the translucent glass 35, is reflected on the lower surface of the continuous paper P, the reflected light, which penetrates the translucent glass 35 again and is incident on the lens barrel 30, is condensed.

As illustrated in FIG. 2, an imaging member 40 is mounted on the lower end of the third lens barrel member 33 by using screws (not illustrated) so as to close an opening section of the lower end of the third lens barrel member 33. The imaging member 40 includes a mounting plate 41 closing the opening section of the lower end of the third lens barrel member 33 and an imaging element 42 as an example of an imaging section provided on the upper surface of the mounting plate 41. Then, the imaging element 42 is disposed in the third lens barrel member 33 in a state where the imaging member 40 is mounted on the third lens barrel member 33.

In this case, the imaging element 42 is disposed in a position farther than the condensing lens 38 with respect to the continuous paper P in the lens barrel 30. The imaging element 42 has an imaging surface 42a on which an image of the lower surface of the continuous paper P, which is condensed by the condensing lens 38, is formed, and is configured of a two-dimensional image sensor, for example. Furthermore, the condensing lens 38 is disposed at a height such that the image of the lower surface of the continuous paper P is formed on the imaging surface 42a of the imaging element 42 and an optical axis passes through the center of the detection window 34 and the center of the imaging surface 42a.

Then, the imaging unit 23 captures the image of a texture (a paper surface pattern) of the lower surface of the continuous paper P supported by the support stand 17, based on the reflected light when irradiating the continuous paper P from the light irradiation section 37. The transportation amount of the continuous paper P per unit time is calculated by comparing two images which are captured before and after at fixed time intervals. In other words, the imaging unit 23 detects the transportation amount of the continuous paper P, based on the reflected light when the light is radiated from the light irradiation section 37 to the continuous paper P.

In addition, flat plate-shaped mounting pieces 43 are protruded into the upper end portion of an outer peripheral surface of the second lens barrel member 32 along the width direction X on both sides in the width direction X, respectively. In this case, in the lens barrel 30, a length of a portion above each of the mounting pieces 43 is shorter than a length of a portion below each of the mounting pieces 43. Then, the mounting pieces 43 are fixed to the lower surface of the support frame 24 by screws 44, respectively. Therefore, a fixed position of each of the mounting pieces 43 with respect to the support frame 24 is a fixed position of the lens barrel 30 with respect to the support frame 24.

In this case, the fixed position of the lens barrel 30 with respect to the support frame 24 is positioned closer than the condensing lens 38 and is positioned farther than the light irradiation section 37 with respect to the continuous paper P. In other words, the lens barrel 30 is fixed to the support frame 24 in a position higher than the condensing lens 38 and lower than the light irradiation section 37.

Next, operation of the ink jet type printer 11 configured as described above will be described below, in particular focusing on operation when the imaging unit 23 detects the transportation amount of the continuous paper P.

Now, as illustrated in FIG. 1, when the continuous paper P is printed upon, the ink is ejected from each nozzle 13a of the recording head 13 onto the continuous paper P which is supported on the support surface 17a while the continuous paper P is transported from the upstream side to the downstream side along the transportation path thereof. At this time, the imaging unit 23 detects the transportation amount of the continuous paper P supported on the support surface 17a in a non-contact manner.

Then, when the transportation amount of the continuous paper P is detected by the imaging unit 23, as illustrated in FIG. 2, first, the light is radiated from the light irradiation section 37 to the lower surface of the continuous paper P through a whole detection window 34. Then, the light radiated on the lower surface of the continuous paper P is reflected on the lower surface of the continuous paper P and the reflected light is condensed in the condensing lens 38 so that the image (the image of the texture) of the lower surface of the continuous paper P is formed on the imaging surface 42a.

The image of the lower surface of the continuous paper P formed on the imaging surface 42a is imaged by the imaging element 42. Then, the transportation amount of the continuous paper P per unit time is calculated (detected) by comparing the two images of the lower surface of the continuous paper P which are captured before and after at fixed time intervals by the imaging element 42. At this time, when an ambient temperature of the lens barrel 30 is increased, the lens barrel 30 is extended in the vertical direction (axial direction) from the fixed position (the height position of each of the mounting pieces 43) as a base point.

In other words, in the lens barrel 30, a whole portion below the fixed position is extended toward a lower side (a direction opposite to the object to be detected) and a whole portion above the fixed position is extended toward an upper side (a direction approaching the object to be detected). In this case, in the lens barrel 30, since the length of the portion above the fixed position is shorter than the length of the portion below the fixed position, an extended length of the below portion is longer than an extended length of the above portion.

Then, in the embodiment, the condensing lens 38 and the imaging element 42 are disposed in positions lower than the fixed position in the lens barrel 30. In addition, since the first lens barrel member 31, the second lens barrel member 32 and the third lens barrel member 33 configuring the lens barrel 30 have the same coefficients of linear expansion as each other, each of members 31, 32 and 33 is extended in the same proportion as each other by the increase in ambient temperature of the lens barrel 30.

Thus, since the condensing lens 38 and the imaging element 42 are moved downward together with the extension of the lens barrel 30, change in a positional relationship between the condensing lens 38 and the imaging element 42 is suppressed. Therefore, since shift of a focus position of the condensing lens 38 is suppressed, degradation of imaging accuracy of the continuous paper P due to the imaging element 42 is suppressed. Accordingly, since degradation of image quality of the two images which are captured before and after at fixed time intervals is suppressed, degradation of detection accuracy of the transportation amount of the continuous paper P, based on the moving amount of texture of the continuous paper P, is suppressed.

The following effect can be obtained by the embodiment described above.

(1) The lens barrel 30 is fixed to the support frame 24 in the position closer to the continuous paper P than the condensing lens 38. Then, when the ambient temperature of the imaging unit 23 (the lens barrel 30) is increased, since the lens barrel 30 is vertically extended from the position which is fixed by the support frame 24 as the base point, the condensing lens 38 and the imaging element 42 are moved toward the lower side away from the continuous paper P according to the extension of the lens barrel 30. Thus, even when the lens barrel 30 is extended due to the increase in the ambient temperature, since change in the positional relationship between the condensing lens 38 and the imaging element 42 is suppressed, it is possible to suppress the shift of the focus position of the condensing lens 38. Therefore, it is possible to suppress the degradation of the imaging accuracy of the continuous paper P due to the imaging element 42.

(2) The lens barrel 30 is configured by bonding the first lens barrel member 31, the second lens barrel member 32 and the third lens barrel member 33, and the coefficients of linear expansion of each of members 31, 32 and 33 are the same as each other. Then, when the ambient temperature of the imaging unit 23 (the lens barrel 30) is increased, each of members 31, 32 and 33 configuring the lens barrel 30 is extended uniformly in the same proportion as each other. Thus, since the positional relationship between the condensing lens 38 and the imaging element 42 is maintained, it is possible to effectively suppress the shift of the focus position of the condensing lens 38. Therefore, even when the lens barrel 30 is configured by bonding each of members 31, 32 and 33, it is possible to suppress the degradation of the imaging accuracy of the continuous paper P due to the imaging element 42.

(3) Since each of members 31, 32 and 33 configuring the lens barrel 30 is configured of the same material as each other, it is possible to easily conform the coefficients of linear expansion of each of members 31, 32 and 33.

MODIFICATION EXAMPLE

In addition, the embodiment described above may be modified as described below.

In the imaging unit 23 of the transportation device 12, the lens barrel 30 may be fixed to the support frame 24 in a position where a distance from the continuous paper P is the same as a distance between the continuous paper P and the light irradiation section 37. Thus, when the ambient temperature of the imaging unit 23 (the lens barrel 30) is increased, since the lens barrel 30 is vertically extended from the position which is fixed by the support frame 24 as the base point, it is possible to reduce the moving amount of the light irradiation section 37 depending on the extension of the lens barrel 30. Therefore, since the change in the distance between the light irradiation section 37 and the continuous paper P can be suppressed, it is possible to suppress the degradation of irradiation accuracy of the light with respect to the continuous paper P due to the light irradiation section 37.

Each of members 31, 32 and 33 configuring the lens barrel 30 may not necessarily be configured of the same material as each other.

Each of members 31, 32 and 33 configuring the lens barrel 30 may not necessarily have the same coefficients of linear expansion as each other.

The fixed position of the lens barrel 30 with respect to the support frame 24 may be positioned closer to the continuous paper P than the light irradiation section 37.

A plurality of condensing lenses 38 may be disposed in the lens barrel 30.

The imaging unit 23 may be disposed so as to face the printing surface of the continuous paper P.

The imaging unit 23 may be fixed to the support stand 17. In this case, the support stand 17 can use a material such as a synthetic resin and is preferably configured of a material having high stiffness, for example, metal.

The object to be detected is not limited to the continuous paper P and may be a single cut sheet.

The object to be detected may be, for example, cloth, plastic film, metal foil or the like if the surface thereof has a texture.

The ink jet type printer 11 may be a serial printer or may be a line printer.

In the embodiments described above, the recording apparatus may be a fluid ejecting apparatus which performs recording by ejecting or discharging fluid (liquid or a liquid material consisting of particles of a functional material dispersed or mixed in a liquid), and a flowing material such as gel (including a solid that may be ejected by flowing as the liquid), other than the ink. For example, it may be a liquid material ejecting apparatus performing the recording by ejecting a liquid material including a material in a dispersed or dissolved form such as an electrode or color material (pixel material) used to produce a liquid crystal display, an electroluminescence (EL) display, and a surface emitting display. In addition, it may be a fluid material ejecting apparatus ejecting a flow material such as gel (for example, physical gel), a powder ejecting apparatus (for example, a toner jet type recording apparatus) ejecting a solid, an example of which is a powder (powder material) such as toner. Then, the invention may be applied to any type of liquid ejecting apparatuses of these. In addition, in the specification, "fluid" is an idea that does not include fluid consisting only of gas, and as the fluid, for example, liquid (including, inorganic solvent, organic solvent, solution, liquid material resin, liquid material metal (liquid metal melt), or the like), liquid material, flow material, powder material (including granules, powder or the like) or the like is included.

The transportation device is not limited to being included in recording apparatus performing the recording process with respect to the object to be detected and may be included in various processing apparatuses performing any process with respect to the object to be detected.

The entire disclosure of Japanese Patent Application No. 2012-242450, filed Nov. 2, 2012 is expressly incorporated by reference herein.

What is claimed is:

1. A transportation device comprising:
   a transportation section that transports an object to be detected, the transportation section including a support stand for the object; and a detection section that detects a transportation amount of the object to be detected which is transported by the transportation section, the detection section being positioned beneath the support stand, wherein the detection section includes:

a case;

a light irradiation section disposed in the case and capable of radiating light on the object to be detected;

an optical member which is disposed in a position below and farther than the light irradiation section from the object to be detected in the case and condenses a reflected light when the light is radiated from the light irradiation section to the object to be detected; and an imaging section which is disposed in a position below and farther than the optical member from the object to be detected in the case and captures an image by receiving the reflected light condensed by the optical member, and wherein the case is fixed to the support stand at a position closer to the object to be detected than the optical member.

2. The transportation device according to claim 1, wherein the case is configured by bonding a plurality of members, and wherein coefficients of linear expansion of each of the members are the same as each other.

3. The transportation device according to claim 2, wherein each of the members is configured of the same material as each other.

4. The transportation device according to claim 1, wherein the case is fixed to a position where a distance from the object to be detected is the same as a distance between the object to be detected and the light irradiation section.

5. A recording apparatus comprising:

the transportation device according to claim 1; and a recording section that performs a recording process with respect to the object to be detected which is transported by the transportation device.

6. A recording apparatus comprising:

the transportation device according to claim 2; and a recording section that performs a recording process with respect to the object to be detected which is transported by the transportation device.

7. A recording apparatus comprising:

the transportation device according to claim 3; and a recording section that performs a recording process with respect to the object to be detected which is transported by the transportation device.

8. A recording apparatus comprising:

the transportation device according to claim 4; and a recording section that performs a recording process with respect to the object to be detected which is transported by the transportation device.

* * * * *